(12) United States Patent
Kato et al.

(10) Patent No.: US 9,636,030 B2
(45) Date of Patent: May 2, 2017

(54) PORTABLE ELECTRONIC APPARATUS

(71) Applicant: Seiko Instruments Inc., Chiba-shi, Chiba (JP)

(72) Inventors: Teruo Kato, Chiba (JP); Hideki Okuda, Chiba (JP); Dai Terasawa, Chiba (JP)

(73) Assignee: SEIKO INSTRUMENTS INC., Chiba (JP)

( * ) Notice: Subject to any disclaimer, the term of this patent is extended or adjusted under 35 U.S.C. 154(b) by 553 days.

(21) Appl. No.: 14/204,168

(22) Filed: Mar. 11, 2014

(65) Prior Publication Data

US 2014/0275931 A1    Sep. 18, 2014

(30) Foreign Application Priority Data

Mar. 12, 2013 (JP) .................. 2013-049551

(51) Int. Cl.
*A61B 5/0408* (2006.01)
*A61B 5/00* (2006.01)
*A61B 5/024* (2006.01)
*A61B 5/0404* (2006.01)

(52) U.S. Cl.
CPC ...... *A61B 5/04085* (2013.01); *A61B 5/02438* (2013.01); *A61B 5/0404* (2013.01); *A61B 5/6831* (2013.01)

(58) Field of Classification Search
CPC .......................... A61B 5/04085; A61B 5/6831
USPC ......................................................... 600/390
See application file for complete search history.

(56) References Cited

U.S. PATENT DOCUMENTS

| | | |
|---|---|---|
| 7,428,433 B2 | 9/2008 | Juan |
| 2013/0096412 A1* | 4/2013 | Kaneko ............. A61B 5/02438 600/390 |

* cited by examiner

*Primary Examiner* — Lee S Cohen
(74) *Attorney, Agent, or Firm* — Brinks Gilson & Lione

(57) ABSTRACT

There is provided a portable electronic apparatus including an apparatus main body that includes electronic components built therein, a fixation belt that is used to attach the apparatus main body to a living body surface, a connector that is provided at an end of the fixation belt in a belt longitudinal direction, and has an engagement protrusion that is detachably stored in an engagement recess formed at the apparatus main body, and a biasing body that is provided in the engagement recess, and biases the engagement protrusion stored in the engagement recess so as to maintain an engagement state between the engagement recess and the engagement protrusion.

10 Claims, 14 Drawing Sheets

FIG. 13
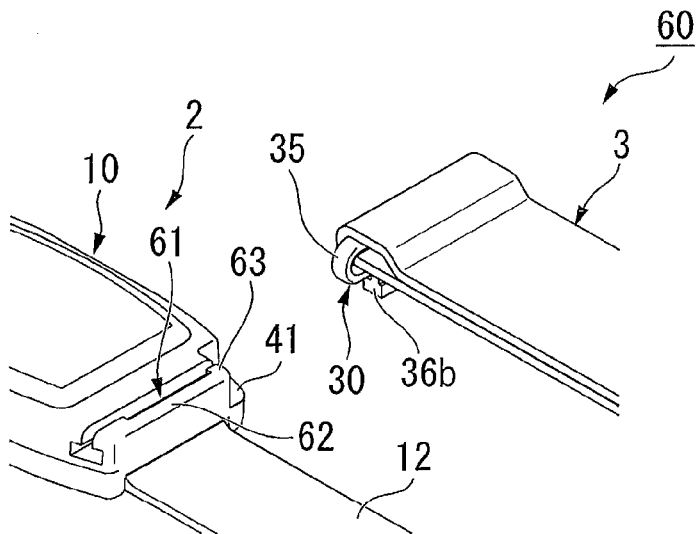
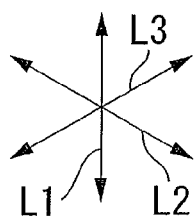
FIG. 14
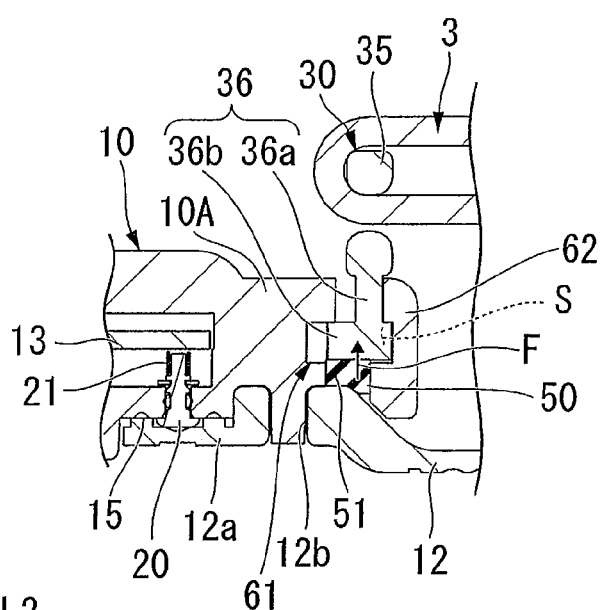
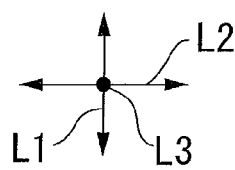

FIG. 19
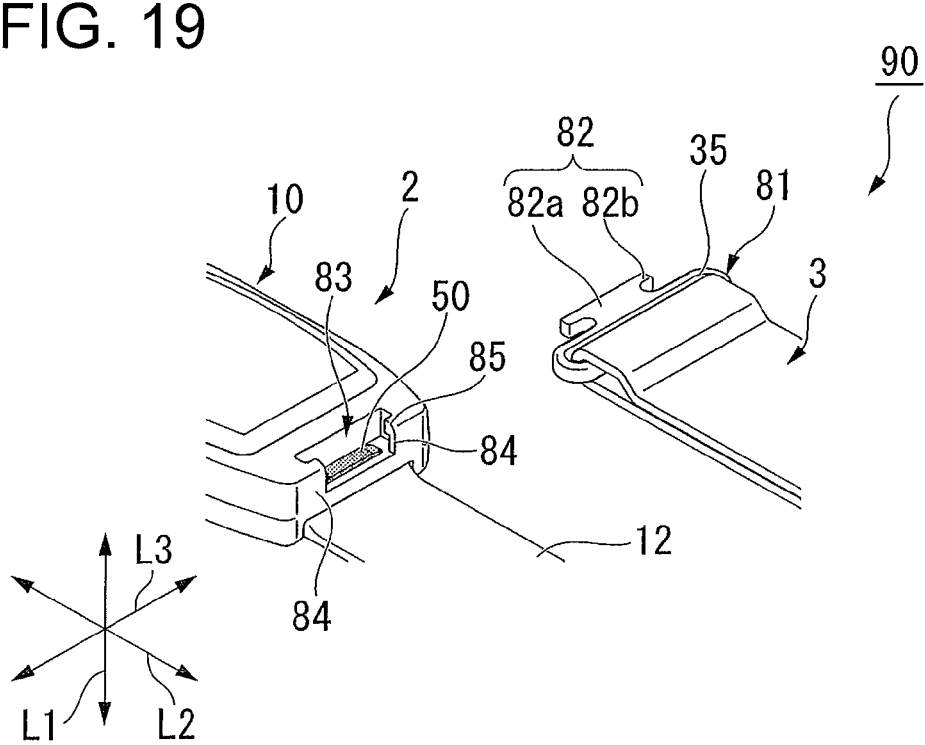
FIG. 20
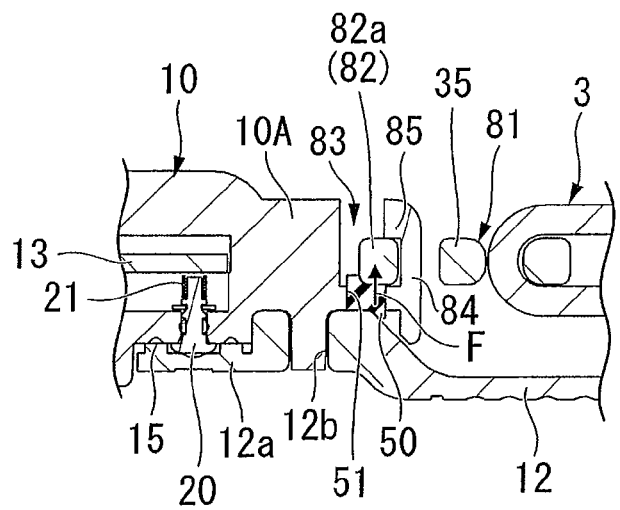
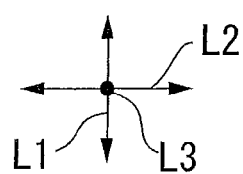

PORTABLE ELECTRONIC APPARATUS

RELATED APPLICATIONS

This application claims priority under 35 U.S.C. §119 to Japanese Patent Application No. 2013-049551 filed on Mar. 12, 2013, the entire content of which is hereby incorporated by reference.

BACKGROUND OF THE INVENTION

Field of the Invention

The present invention relates to a portable electronic apparatus attached to a living body.

Background Art

As one of portable electronic apparatuses attached to a living body, there is a biological information detection apparatus in which electrodes are attached to a living body surface and a biological signal is detected. For example, there is a heart rate measurement apparatus which detects an electrocardiographic signal which occurs due to heartbeats so as to measure a heart rate from a living body surface (for example, refer to the specification of U.S. Pat. No. 7,428, 433).

A heart rate measurement apparatus disclosed in the specification of U.S. Pat. No. 7,428,433 includes an apparatus main body and an attachment belt for attaching the apparatus main body to the chest.

The attachment belt is provided with electrodes which detect a heart rate, and a connection member which outputs a detection signal to a communication circuit of the apparatus main body. The connection member protrudes from an end member provided at an end of the attachment belt toward the apparatus main body side, and is removably engaged with a connection recess formed in the apparatus main body. In addition, the connection member is slidably inserted into the connection recess and is engaged therewith. Therefore, the apparatus main body is mechanically connected to the attachment belt, and the electrodes are electrically connected to the communication circuit.

In addition, in the heart rate measurement apparatus, in order to maintain the engagement state between the connection member and the connection recess, a hemispherical protrusion protrudes from the end member toward the apparatus main body, and the protrusion is engaged with a hemispherical recess formed in the apparatus main body side. The engagement between the protrusion and the recess prevents the connection member from being released out of the connection recess.

SUMMARY OF THE INVENTION

However, when the heart rate measurement apparatus is attached, an external force (tensile force) tends to be applied to the attachment belt in a longitudinal direction thereof. In this case, the above-described protrusion and recess are respectively located at protruding and dented places of the attachment belt in the longitudinal direction, and are thus moved so as to be separated from each other by the external force. For this reason, an engagement amount between the protrusion and the recess is reduced, and thus looseness easily occurs between the apparatus main body and the attachment belt.

Accordingly, there is a case where attachment stability of the apparatus main body is reduced, and it is difficult to perform accurate heart rate measurement. In addition, depending on cases, there is a probability that the engagement between the protrusion and the recess may be released, and thus the connection member may be abruptly released out of the connection recess, and thus there is a concern that heart rate measurement cannot be performed.

The present invention has been made in consideration of these circumstances, and an object thereof is to provide a portable electronic apparatus which can improve an attachment performance and enable an apparatus main body to be properly operated by preventing looseness or abrupt detachment of the apparatus main body.

The present invention provides the following means in order to solve the problems.

(1) According to an aspect of the present invention, there is provided a portable electronic apparatus including an apparatus main body that includes electronic components built therein; a fixation belt that is used to attach the apparatus main body to a living body surface; a connector that is provided at an end of the fixation belt in a belt longitudinal direction; an engagement recess that is formed at one of the apparatus main body and the connector; an engagement protrusion that is formed at the other of the apparatus main body and the connector and is detachably stored in the engagement recess; and a biasing body that is provided at one of the engagement recess and the engagement protrusion, and biases the engagement protrusion stored in the engagement recess so as to maintain an engagement state between the engagement recess and the engagement protrusion.

According to the portable electronic apparatus related to the aspect of the present invention, the engagement protrusion provided at the connector is stored in the engagement recess so as to be engaged therewith. Thus, the fixation belt can be connected to the apparatus main body, and thus the apparatus main body can be attached to the living body surface. In this case, the biasing body provided in the engagement recess biases the engagement protrusion so as to maintain an engagement state between the engagement recess and the engagement protrusion. For this reason, even if an external force such as a tensile force is applied to the fixation belt in the belt longitudinal direction during attachment of the apparatus main body, the biasing body presses the engagement protrusion toward the engagement recess, and thus it is possible to maintain an engagement state between the engagement recess and the engagement protrusion so as to prevent looseness thereof.

Therefore, there is a low probability that looseness or abrupt detachment of the apparatus main body may occur, and thus the apparatus main body can be stably attached to the living body surface, unlike in the related art. Accordingly, it is possible to improve an attachment performance of the portable electronic apparatus, and to properly operate the apparatus main body.

(2) In the aspect, preferably, an allowable space that allows the engagement protrusion stored in the engagement recess to be moved in the belt longitudinal direction is formed in the engagement recess. In addition, preferably, the apparatus main body includes a first restraint wall that restrains the engagement protrusion moved to the allowable space from being further moved in the belt longitudinal direction so as to make the engagement protrusion remain in the allowable space; and a second restraint wall that restrains the engagement protrusion moved to the allowable space from being moved to an opened side of the engagement recess.

In this case, if an external force such as a tensile force is applied to the fixation belt in the belt longitudinal direction during attachment, the engagement protrusion is deviated in the engagement recess in the belt longitudinal direction so as to be moved to the inside of the allowable space. Then, the engagement protrusion comes into contact with the first restraint wall and a further movement thereof is restrained, and thus the engagement protrusion can be made to reliably remain in the allowable space. In addition, at this time, the engagement protrusion is restrained from being moved to the opened side of the engagement recess by the second restraint wall, and thus it is possible to physically prevent the engagement protrusion from being released out of the engagement recess.

As mentioned above, it is possible to reliably prevent the apparatus main body from being detached by reversely using the external force applied in the belt longitudinal direction.

(3) In the aspect, preferably, the biasing body biases the engagement protrusion in a direction different from the belt longitudinal direction.

In this case, since the biasing body biases the engagement protrusion in a direction different from the belt longitudinal direction, even if an external force such as a tensile force is applied to the fixation belt in the belt longitudinal direction during attachment of the apparatus main body, the belt longitudinal direction is different from the biasing direction, and thus it is possible to prevent looseness of the engagement recess and the engagement protrusion while maintaining the engagement state therebetween. Therefore, it is possible to further reduce a probability that looseness or abrupt detachment of the apparatus main body may occur.

(4) In the aspect, preferably, the biasing body biases the engagement protrusion toward the second restraint wall.

In this case, the engagement protrusion can be pressed toward the second restraint wall, and it is possible to further reliably maintain an engagement state between the engagement recess and the engagement protrusion by using the pressing force at this time.

(5) In the aspect, preferably, a biasing direction of the biasing body, a direction in which the engagement protrusion is stored in the engagement recess, and the belt longitudinal direction have a relationship of being perpendicular to each other.

In this case, since the biasing direction of the biasing body, the direction in which the engagement protrusion is stored in the engagement recess, and the belt longitudinal direction have a relationship of being perpendicular to each other, it is possible to more effectively achieve the operation and effect in which looseness or abrupt detachment of the apparatus main body is reliably prevented.

(6) In the aspect, the portable electronic apparatus preferably further includes a pair of electrode members that is installed at the apparatus main body so as to be in contact with the living body surface; and a biological information detection unit that is provided inside the apparatus main body, and detects biological information on the basis of a potential difference occurring between the pair of electrode members.

In this case, the portable electronic apparatus can be suitably used as, for example, a heart rate measurement apparatus, a pedometer, or the like. Particularly, since the apparatus main body can be stably attached to a living body surface, a heart rate or the like can be stably measured with high accuracy.

(7) In the aspect, preferably, the electrode member is made of an elastic material, and the biasing body is pinched between the engagement protrusion stored in the engagement recess and the electrode member.

In this case, since the biasing body is pinched between the engagement protrusion and the elastic electrode member, the engagement protrusion can be biased by also using an elastic force of the electrode member. Therefore, a biasing force can be adjusted without changing a size and the like of the biasing body and without increasing the number of components, and thus the apparatus main body can be more stably attached.

(8) In the aspect, preferably, the biasing body is exchangeably provided in the engagement recess.

In this case, even if the biasing body is worn out or the like, the biasing body need only to be changed, and thus it is possible to reduce maintenance costs.

According to the aspect of the present invention, it is possible to provide a portable electronic apparatus which can improve an attachment performance and enable an apparatus main body to be properly operated by preventing looseness or abrupt detachment of the apparatus main body.

BRIEF DESCRIPTION OF THE DRAWINGS

FIG. 13 is a diagram illustrating a second embodiment according to the present invention, and is a perspective view illustrating a state in which an apparatus main body is disconnected from a fixation belt.

FIG. 14 is a cross-sectional view illustrating a state in which the apparatus main body and the fixation belt illustrated in FIG. 13 are connected to each other.

FIG. 19 is a diagram illustrating a fifth embodiment according to the present invention, and is a perspective view illustrating a state in which an apparatus main body is disconnected from a fixation belt.

FIG. 20 is a cross-sectional view illustrating a state in which the apparatus main body and the fixation belt illustrated in FIG. 19 are connected to each other.

DETAILED DESCRIPTION OF THE PREFERRED EMBODIMENTS

Hereinafter, embodiments according to the present invention will be described with reference to the drawings.

In addition, in the present embodiments, a heart rate measurement apparatus that measures heart rate information which is biological information will be described as an example of a portable electronic apparatus.

First Embodiment

Configuration of Heart Rate Measurement Apparatus

Figure 1:
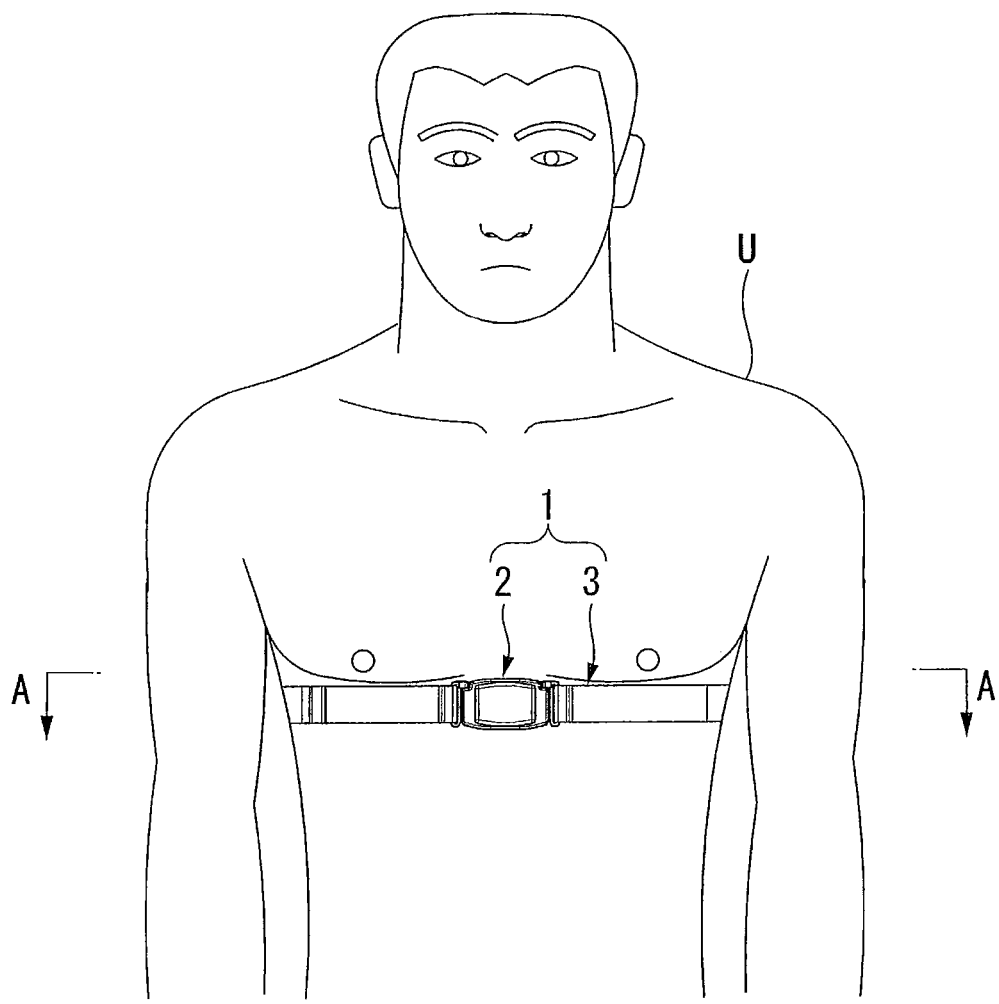
FIG. 1 is a diagram illustrating a first embodiment according to the present invention, and is an attachment diagram illustrating a state in which a heart rate measurement apparatus is attached to the chest of a user.
Figure 2:
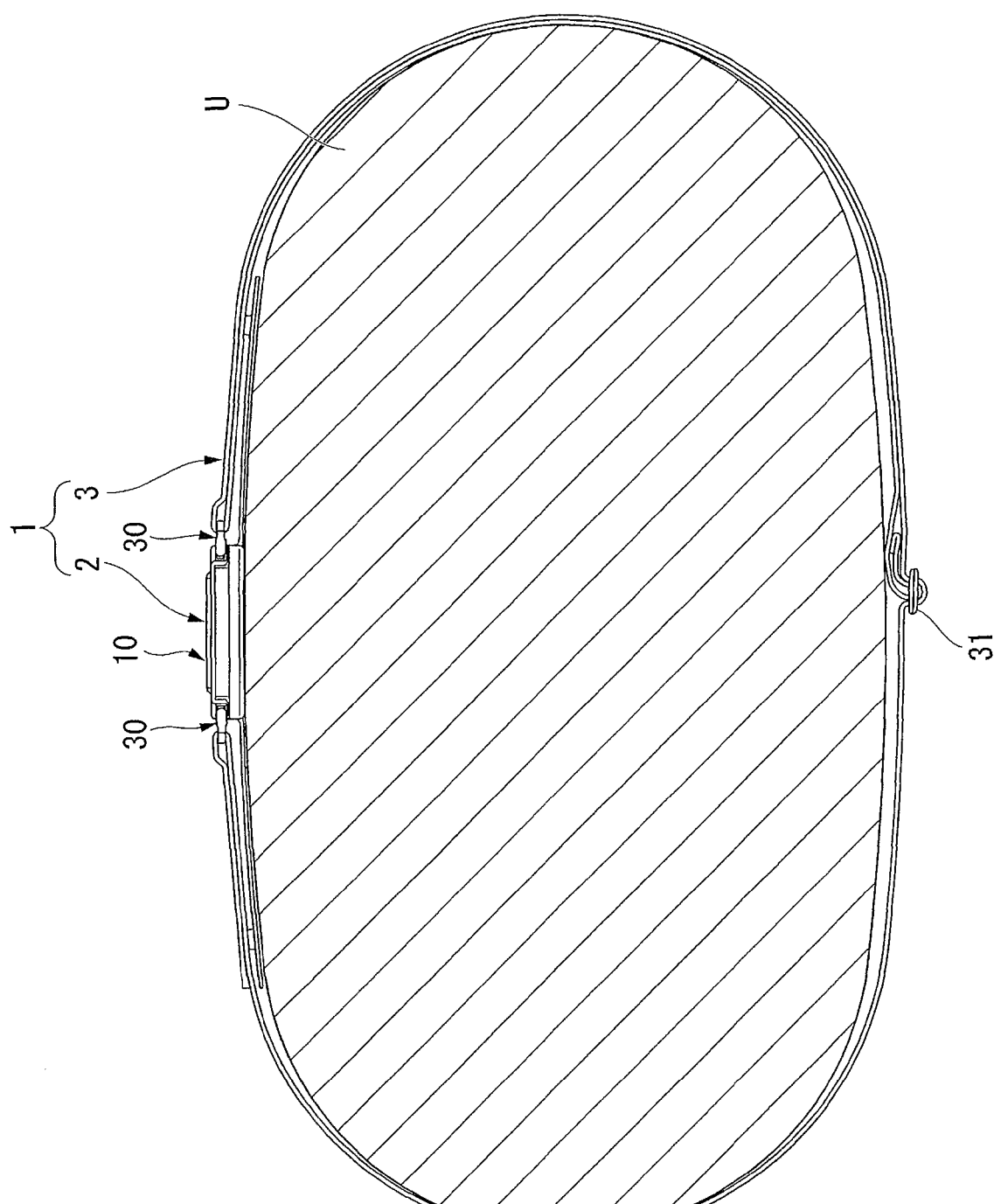
FIG. 2 is a cross-sectional view taken along the line A-A illustrated in FIG. 1.

As illustrated in FIGS. 1 and 2, a heart rate measurement apparatus 1 of the present embodiment is an apparatus which is attached to a living body surface (body surface) on the chest of a user U, detects an electrocardiographic signal occurring due to heartbeats, and detects the detected electrocardiographic signal as heart rate information.

As illustrated in FIGS. 3 to 6, the heart rate measurement apparatus 1 is a portable electronic apparatus which has various built-in electronic components 25 including a detection circuit unit (a biological information detection unit related to the present invention) 26 described later, includes an apparatus main body 2 which is long in a circumferential direction of the chest and a fixation belt 3 which is connected to both ends of the apparatus main body 2 in the longitudinal direction and attaches the apparatus main body 2 to the living body surface, and is operated by power from a button battery 4.

In addition, the button battery 4 also includes a battery called a coin battery, and indicates a so-called disc-shaped battery.

In the following description, when each constituent element of the heart rate measurement apparatus 1 is described, a vertical direction is defined by setting a side adjacent to the chest of the user U to a downward direction, and setting a direction which is opposite thereto and is separated from the user U to an upward direction. In addition, a direction along the vertical direction is a direction perpendicular to the living body surface, and is thus referred to as a normal line direction L1 in some cases.

Further, a direction along the longitudinal direction of the fixation belt 3 is referred to as a belt longitudinal direction L2, and a direction along the width direction is referred to as a belt width direction L3.

Apparatus Main Body

Apparatus main body 2 includes a case 10 that is formed in a rectangular shape in a plan view so as to be long in the circumferential direction of the chest and has a specific thickness in the normal line direction L1; a rear plate 11 that covers the case 10 from the lower side; and a pair of conductive belts (electrode members related to the present invention) 12.

Figure 6:
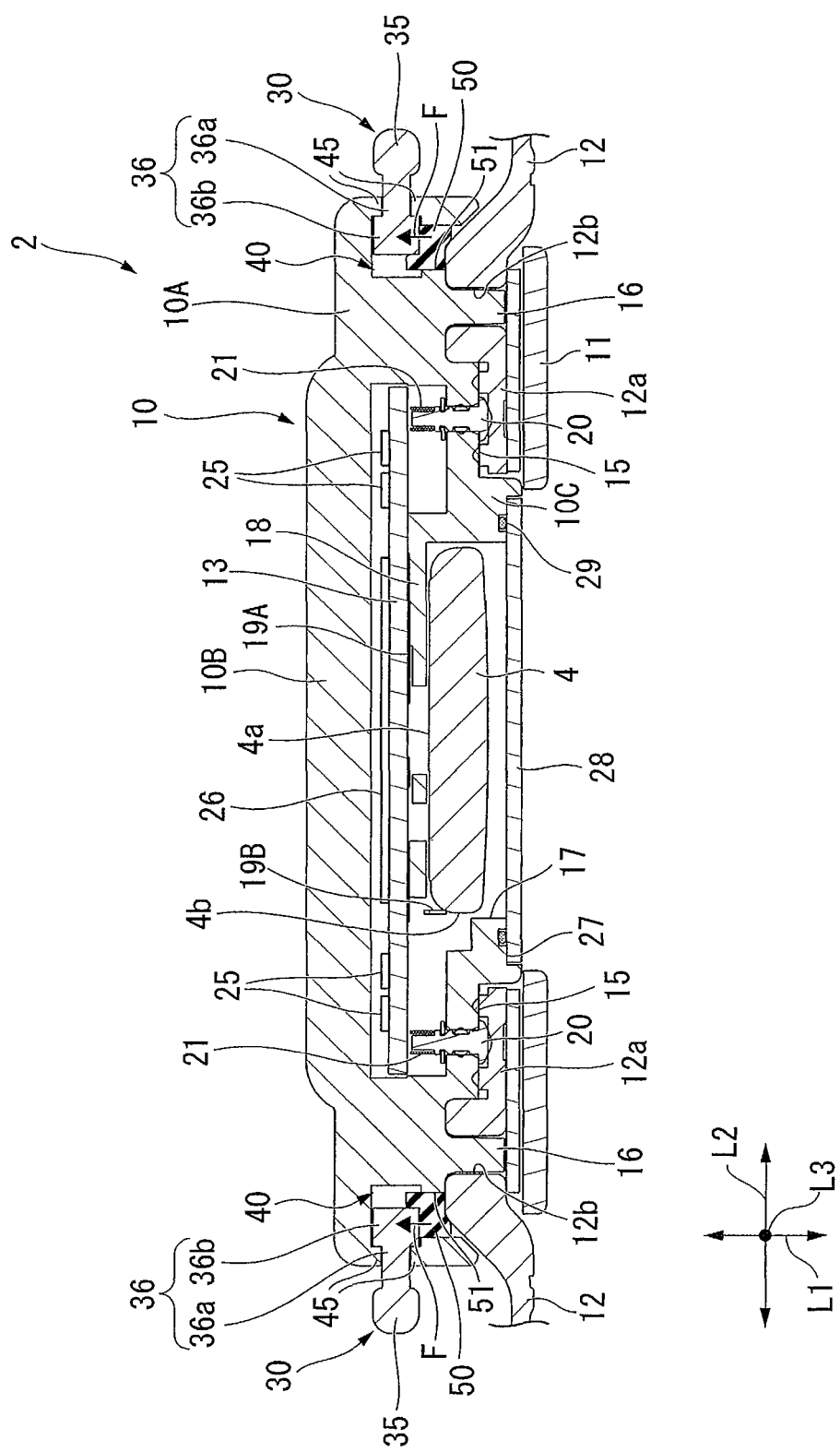
FIG. 6 is a cross-sectional view taken along the line B-B illustrated in FIG. 5.

The case 10 has a frame-shaped outer wall 10A, an upper wall 10B connected to the outer wall 10A, and a bottom wall 10C, which are integrally formed, as illustrated in FIG. 6. A circuit board 13, the button battery 4, and the like are incorporated into an inner space which is demarcated by the outer wall 10A, the upper wall 10B, and the bottom wall 10C.

Step difference portions 15 which are formed to be recessed upward and are opened in the longitudinal direction of the case 10 are formed from the outer wall 10A to the bottom wall 10C at parts located at both ends of the case 10 in the longitudinal direction, and the pair of conductive belts 12 are attached by using the step difference portions 15. In addition, pin-shaped positioning protrusions 16 protrude downward at the parts where the step difference portions 15 are formed in the outer wall 10A.

A battery insertion hole 17 which allows the button battery 4 to be taken in and out and has a circular shape in a plan view is formed at a central part of the bottom wall 10C.

In addition, a battery stage 18 is integrally formed with the bottom wall 10C. The battery stage 18 is located on the upper side of the battery insertion hole 17, positions the button battery 4 inserted through the battery insertion hole 17, and is in contact with a negative pole surface 4a of the button battery 4. The battery stage 18 is provided with a negative terminal member 19A which is in contact with the negative pole surface 4a of the button battery 4 and is electrically connected thereto, and a positive terminal member 19B which is in contact with a positive pole surface (outer circumferential surface) 4b of the button battery 4 and is electrically connected thereto. Further, the negative terminal member 19A and the positive terminal member 19B are formed by, for example, thin metal plate-pressed components.

Figure 3:
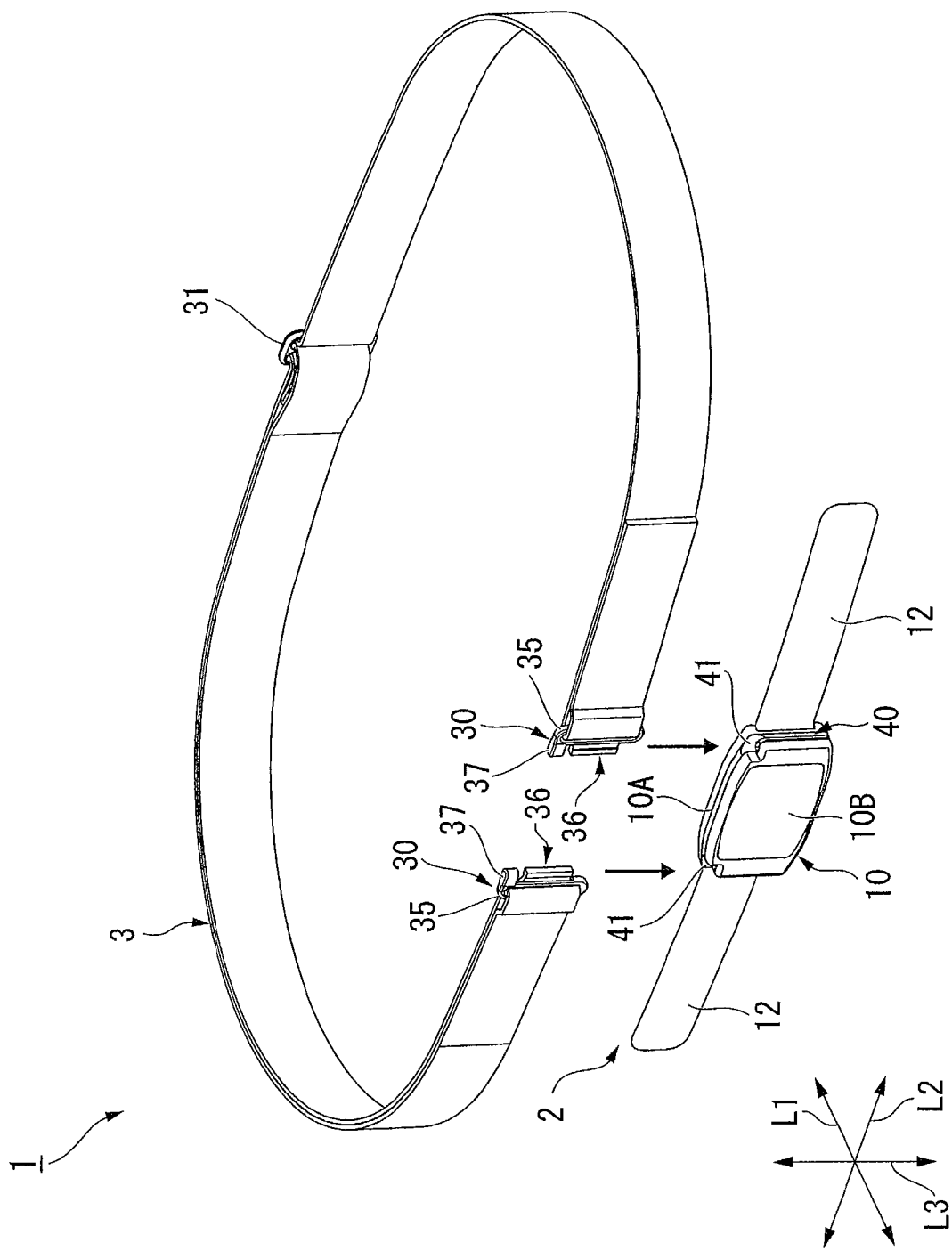
FIG. 3 is a perspective view of the heart rate measurement apparatus illustrated in FIG. 1, and is a diagram illustrating a state in which an apparatus main body is disconnected from a fixation belt.

The pair of conductive belts 12 functions as electrodes which are in contact with the living body surface on the chest of the user U so as to detect a potential difference between both conductive belts and output the potential difference as an electrocardiographic signal, and is formed in a strip shape extending in the circumferential direction of the chest in the illustrated example (refer to FIG. 3).

The conductive belt 12 is a belt made of an elastic material. For example, the conductive belt is made of conductive elastomer. The conductive elastomer may include, for example, a conductive silicon rubber compounded with carbon black, a conductive rubber compounded with carbon black, a conductive polyurethane rubber compounded with carbon black, and the like.

Of both ends of the conductive belt 12 in the longitudinal direction, the end on the apparatus main body 2 side is a circuit connection portion 12a. The pair of conductive belts 12 is installed in the apparatus main body 2 and is electrically connected to the circuit board 13 via the circuit connection portions 12a.

Specifically, a through hole 12b is formed at the circuit connection portion 12a, and the circuit connection portion 12a overlaps the step difference portion 15 in a state in which the positioning protrusion 16 is inserted into the through hole 12b. In addition, the rear plate 11 is fixed to the bottom wall 10C of the case 10 by a fastening member such as a screw (not illustrated), in a state of overlapping a lower surface side of the circuit connection portion 12a. Accordingly, the circuit connection portion 12a is pinched between the step difference portion 15 and the rear plate 11.

With this configuration, the pair of conductive belts 12 is installed in the apparatus main body 2 via the circuit connection portions 12a.

In addition, pin-shaped conduction members 20 are installed at the step difference portions 15. Coil springs 21 which are in contact with the lower surface of the circuit board 13 are externally inserted into upper ends of the conduction members 20 in a compression state. Accordingly, the circuit connection portions 12a are electrically connected to the circuit board 13 via the conduction members and the coil springs 21.

With this configuration, the pair of conductive belts 12 is electrically connected to the circuit board 13 via the circuit connection portions 12a and the coil springs 21.

The circuit board 13 is a board on which various electronic components necessary in heart rate measurement are mounted, and is fixed to the battery stage 18 in a state of being placed thereon. Electrode connection patterns (not illustrated) are formed at the positions corresponding to the coil springs 21 on the lower surface of the circuit board 13 which is thus electrically connected to the circuit connection portions 12a via the coil springs 21. In addition, power supply circuit patterns (not illustrated) which are electrically connected to the negative terminal member 19A and the positive terminal member 19B are formed on the lower surface of the circuit board 13, and thus power is supplied thereto from the button battery 4.

In addition, a detection circuit unit 26, which measures a heart rate on the basis of an electrocardiographic signal detected by the conductive belts 12, is formed on the upper surface of the circuit board 13 in a state of being electrically connected to the electrode connection patterns. It is possible to measure heart rate information of the user U by using a measurement result by performed the detection circuit unit 26.

An antenna unit (not illustrated) which outputs the heart rate information to an external device may be mounted on the circuit board 13. In this case, for example, it is possible to acquire the heart rate information in real time at a position apart from the user U without detaching the heart rate measurement apparatus 1 from the user U.

Annular step portions 27 which surround the battery insertion hole 17 from the outside in a diameter direction are formed at the bottom wall 10C of the case 10. A battery lid 28 is attachably and detachably fixed to the step portions, for example, in a bayonet manner, so as to shield the battery insertion hole 17 by using the step portions 27. In addition, O-rings 29 are installed at the step portions 27 so as to prevent dust or the like from entering the battery insertion hole 17.

Fixation Belt

Figure 4:
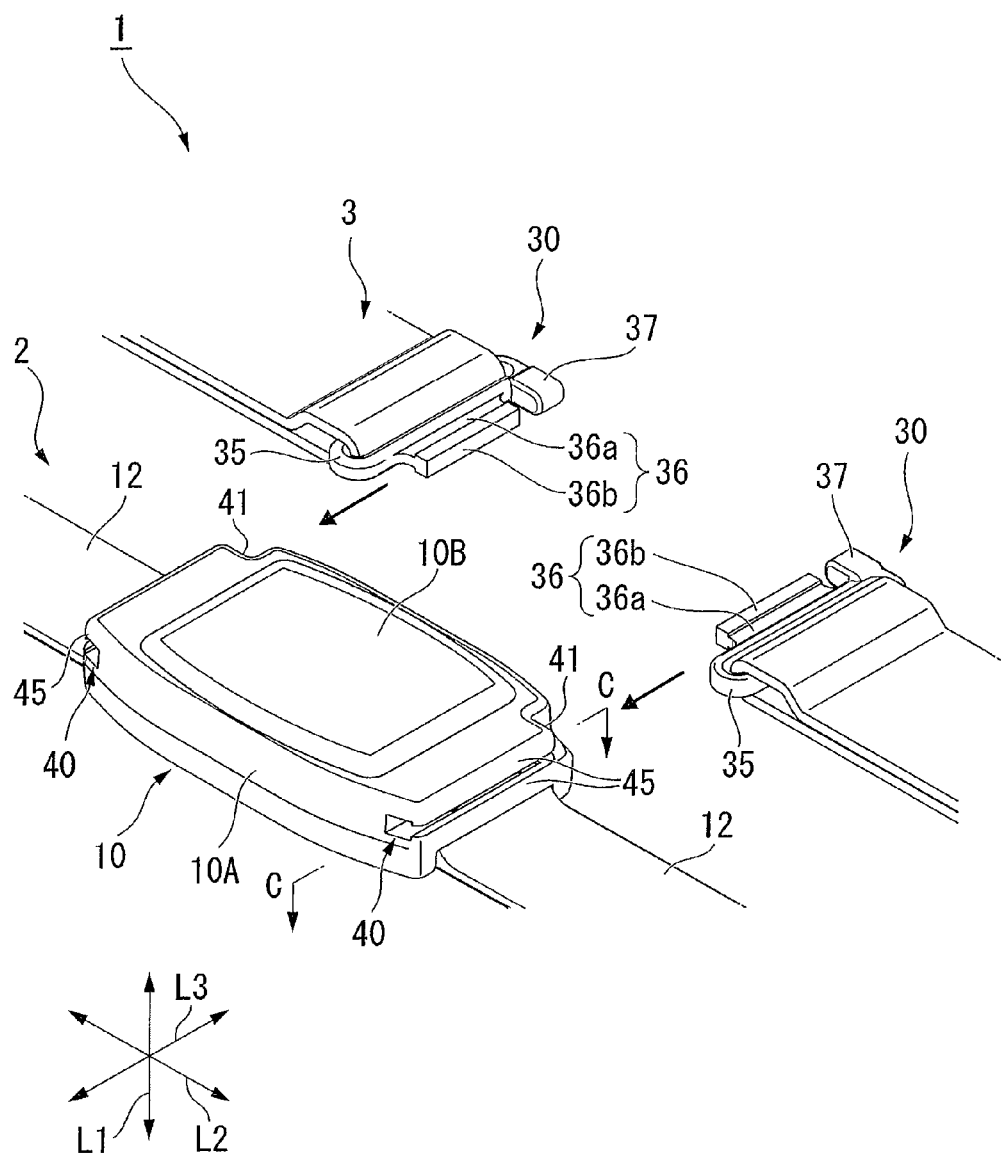
FIG. 4 is an enlarged perspective view of a periphery of the apparatus main body illustrated in FIG. 3.

As illustrated in FIGS. 3 and 4, the fixation belt 3 is a long strip-shaped belt which extends in the circumferential direction of the chest, and is provided with connectors 30 which are connected to the apparatus main body 2 so as to be detached therefrom in a one-touch manner at both ends in the belt longitudinal direction L2.

By using the pair of connectors 30, the fixation belt 3 is connected to the apparatus main body 2, and thus the heart rate measurement apparatus 1 can be easily attached to the chest of the user U (refer to FIG. 1), or the fixation belt 3 is disconnected from the apparatus main body 2, and thus the heart rate measurement apparatus 1 can be easily detached from the chest of the user U.

In the present embodiment, both of the pair of connector 30 have the same configuration, but are not limited thereto.

As illustrated in FIG. 3, the fixation belt 3 is provided with an adjuster 31 which allows a length of the fixation belt 3 to be arbitrarily adjusted. A length adjusting method using the adjuster 31 is common, and thus detailed description thereof will be omitted. In addition, the fixation belt 3 is made of a rubber material such as, for example, elastic urethane.

Figure 5:
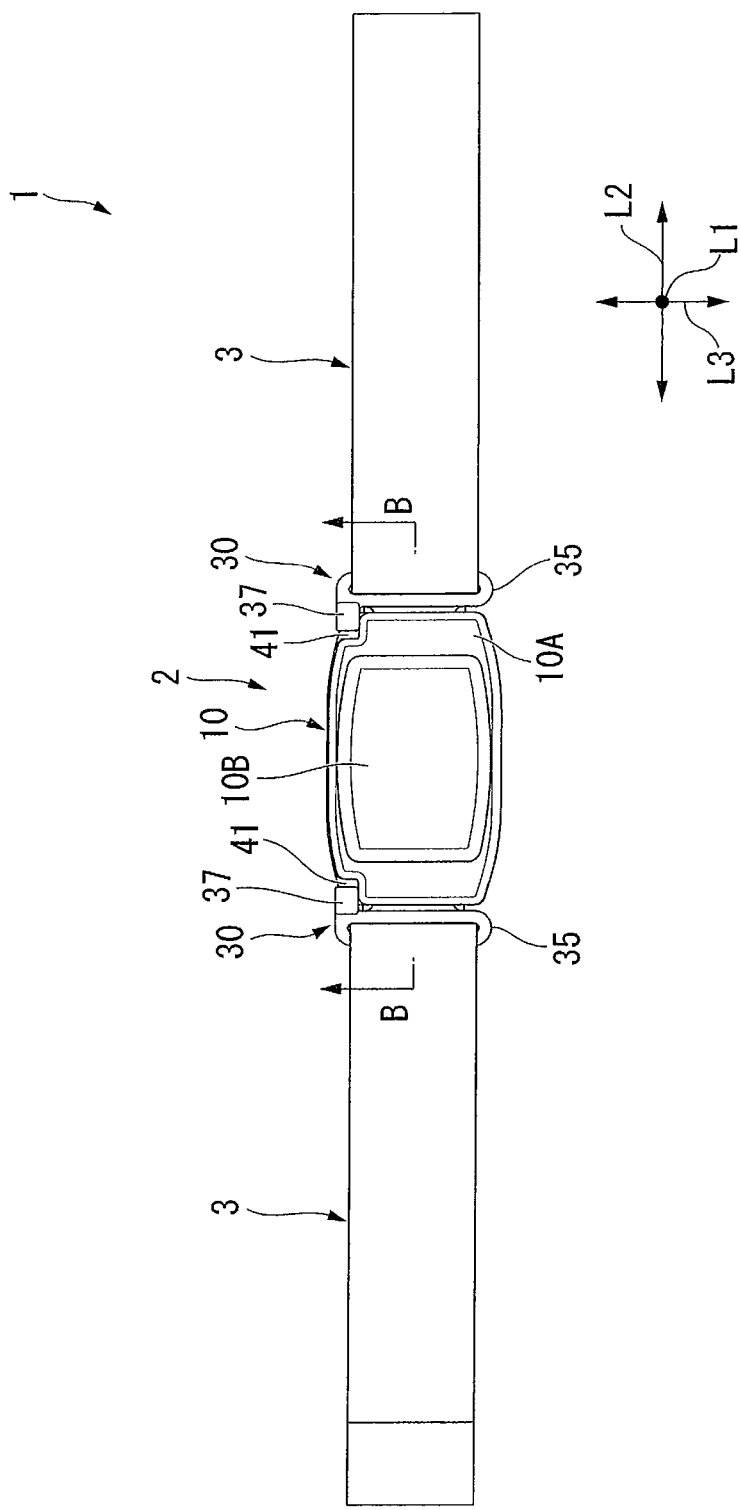
FIG. 5 is a front view of the heart rate measurement apparatus illustrated in FIG. 1, and is a diagram illustrating a state in which the apparatus main body is connected to the fixation belt.

As illustrated in FIGS. 4 to 6, the connector 30 includes an annular ring 35 which is installed so that the fixation belt 3 is folded, and an engagement protrusion 36 and a stopper 37 which protrude toward the apparatus main body 2 side from the annular ring 35 in the belt longitudinal direction L2.

In addition, in the present embodiment, the connector 30 is provided with the stopper 37 but is not limited thereto. In other words, the stopper 37 is not an essential constituent element, and may be omitted.

The engagement protrusion 36 is a member which is detachably stored in an engagement recess 40 described later formed at the apparatus main body 2 side through sliding in the belt width direction L3.

Specifically, the engagement protrusion 36 includes a protrusion piece 36a whose base end is integrally formed with the annular ring 35 and which has a rectangular plate shape in a plan view so as to be long in the belt width direction L3 and short in the belt longitudinal direction L2; and a claw 36b which is formed at a front end of the protrusion piece 36a and is swollen upward and downward.

The stopper 37 is integrally formed with the annular ring 35 so as to be disposed with a gap with respect to the engagement protrusion 36 in the belt width direction L3 and to protrude in parallel to the engagement protrusion 36. In this case, a protrusion extent of the stopper 37 is equivalent to a protrusion extent of the engagement protrusion 36. In addition, the stopper 37 in the normal line direction L1 is formed to be thicker than the claw 36b.

Connection Structure of Apparatus Main Body to Fixation Belt

The engagement recesses 40 in which the engagement protrusions 36 are detachably stored are respectively formed at the parts located at both ends of the case 10 in the longitudinal direction in the outer wall 10A of the case 10 of the apparatus main body 2.

As illustrated in FIGS. 2, 4 and 6, the engagement recess 40 is formed at the part located further upward than the step difference portion 15 in the outer wall 10A of the case 10, and is formed in a tunnel shape in the belt width direction L3. In this case, the engagement recess 40 is also opened at the side surface which faces the belt longitudinal direction L2 in the outer wall 10A.

In addition, in the present embodiment, the engagement recess 40 is formed at the part located further upward than the step difference portion 15 but is not limited thereto.

Accordingly, the engagement protrusion 36 can be stored in the engagement recess 40 through sliding in the belt width direction L3. In addition, the engagement recess 40 has a height (depth) in the normal line direction L1 which is slightly larger than a thickness of the claw 36b of the engagement protrusion 36 and has an enough size to store the claw 36b without rattling.

In addition, dents 41 which are dented downward are formed at corners of the case 10, and the stoppers 37 are stored in the dents 41 when the engagement protrusions 36 are stored in the engagement recesses 40 (refer to FIG. 5).

In other words, in the present embodiment, the engagement protrusions 36 are inserted into the engagement recesses 40 from the side on which the dents 41 are formed, in the belt width direction L3 through sliding, and the sliding is restrained at the time when the stoppers 37 come into contact with the case 10. Accordingly, since the engagement protrusions 36 are positioned in the engagement recesses 40 in the belt width direction L3, and the stoppers 37 are stored in the dents 41, the stoppers 37 are prevented from falling out of the case 10.

In addition, in the present embodiment, the dents 41 are opened toward the upper side of the case 10 but is not limited thereto.

Figure 7:
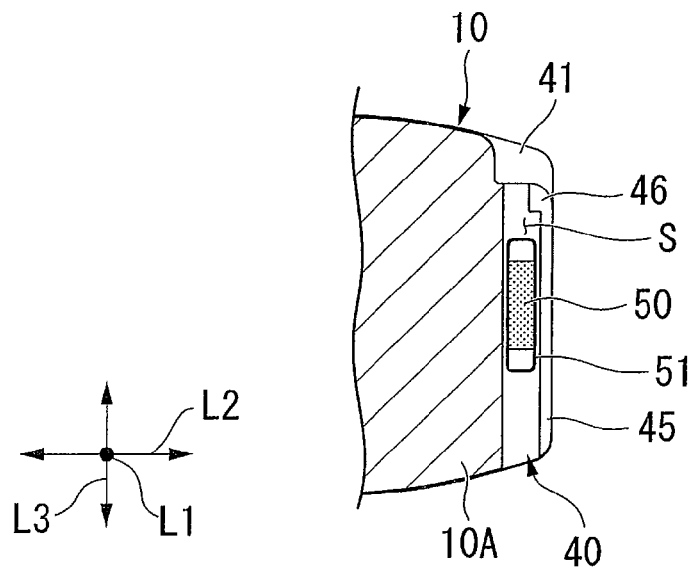
FIG. 7 is a cross-sectional view taken along the line C-C illustrated in FIG. 4.
Figure 8:
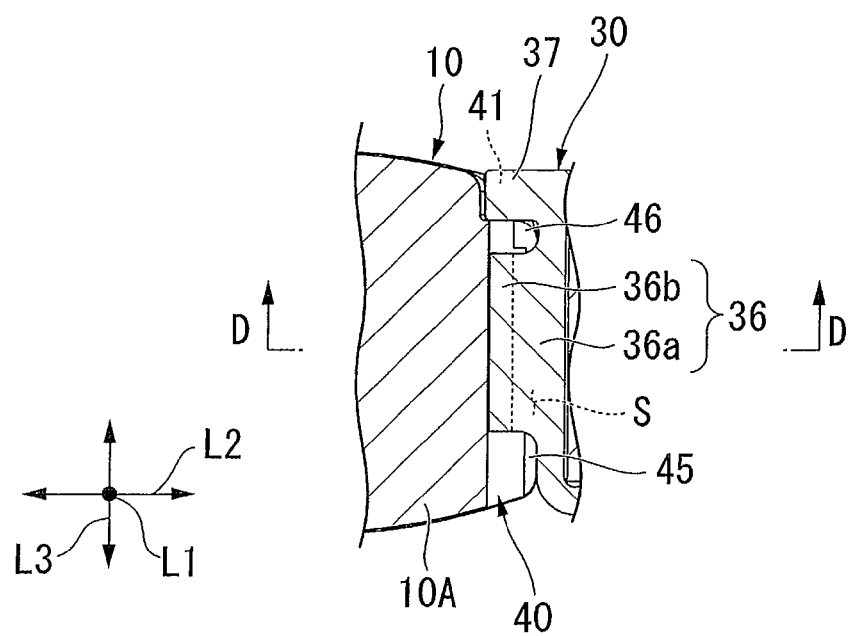
FIG. 8 is a cross-sectional view illustrating a state in which an engagement protrusion is stored in an engagement recess in the state illustrated in FIG. 7.
Figure 9:
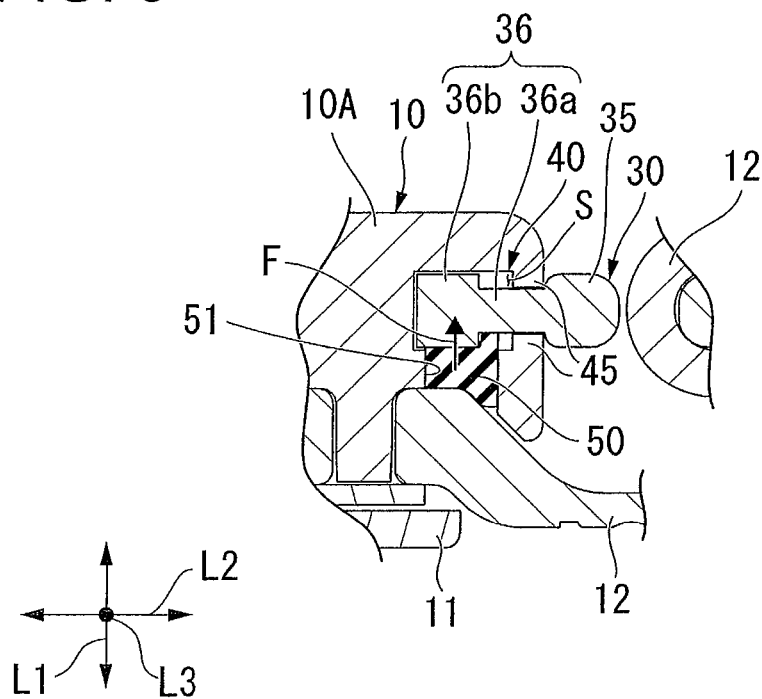
FIG. 9 is a cross-sectional view taken along the line D-D illustrated in FIG. 8.

As illustrated in FIGS. 7 to 9, an allowable space S, which allows the engagement protrusion 36 stored in the engagement recess 40 to be moved in the belt longitudinal direction L2, is formed in the engagement recess 40. Specifically, when the engagement protrusion 36 is stored in the engagement recess 40, the allowable space S is formed so as to allow the engagement protrusion 36 to be separated from the apparatus main body 2 in the belt longitudinal direction L2.

Figure 10:
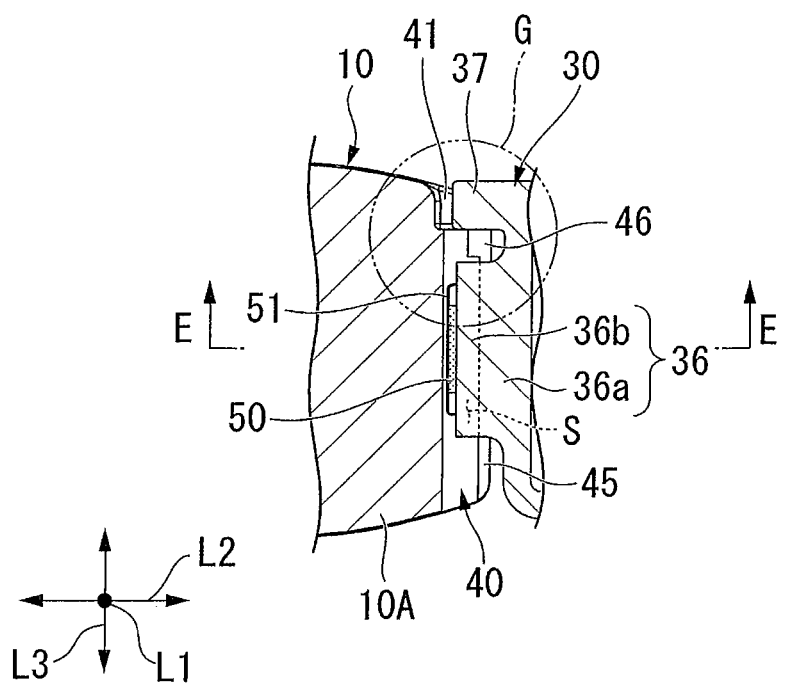
FIG. 10 is a cross-sectional view illustrating a state in which the engagement protrusion is deviated in a belt longitudinal direction in the state illustrated in FIG. 9.
Figure 11:
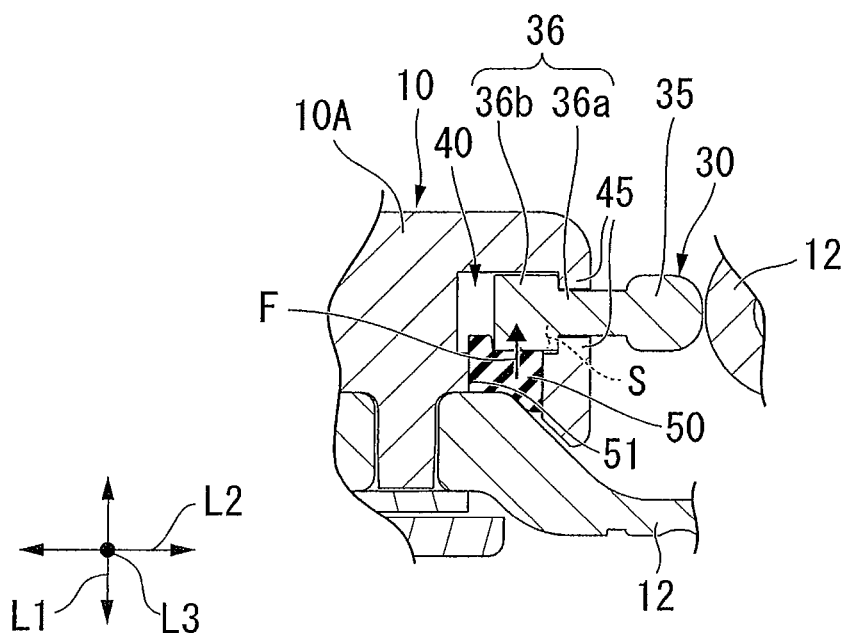
FIG. 11 is a cross-sectional view taken along the line E-E illustrated in FIG. 10.
Figure 12:
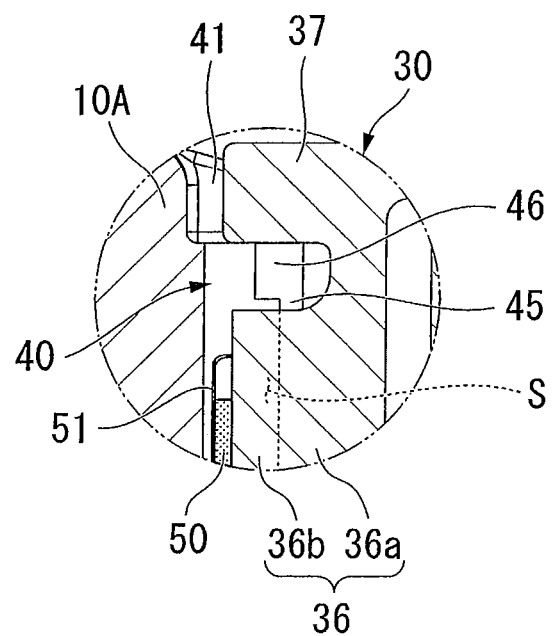
FIG. 12 is an enlarged view of a two-dot chain line G part illustrated in FIG. 10.

On the other hand, as illustrated in FIGS. 10 to 12, first restraint walls 45 and a second restraint wall 46 are formed at the outer wall 10A of the case 10. The first restraint walls 45 restrain the engagement protrusion 36 moved in the allowable space S from being further moved in the belt longitudinal direction L2 so as to make the engagement protrusion 36 remain in the allowable space S, and the second restraint wall 46 restrains the engagement protrusion 36 moved in the allowable space S from being reversely moved in the belt width direction L3 and moved toward the opened side of the engagement recess 40.

The first restraint walls 45 are formed along the opened part of the engagement recess 40 which is opened in the belt longitudinal direction L2, and protrude upward and downward so as to be formed with the protrusion piece 36a of the engagement protrusion 36 vertically interposed therebetween. Accordingly, the claw 36b of the engagement protrusion 36 is brought into contact with the first restraint walls 45, thereby restraining a further movement thereof in the belt longitudinal direction L2.

The second restraint wall 46 is formed so as to protrude in a direction perpendicular to the first restraint walls 45 toward the inside of the engagement recess 40 on the dent 41 side of the first restraint walls 45. Accordingly, a side surface of the claw 36b of the engagement protrusion 36 can be engaged with an inner wall surface of the second restraint wall 46 through contact, and thus it is possible to restrain the engagement protrusion 36 from being released out of the engagement recess 40. In addition, an outer wall surface of the second restraint wall 46 functions as a contact surface which is in contact with the stopper 37.

In addition, as illustrated in FIGS. 6 and 7, a biasing body 50, which biases the engagement protrusion 36 stored in the engagement recess 40 in a direction different from the belt longitudinal direction L2 so as to maintain an engagement state between the engagement recess 40 and the engagement protrusion 36, is provided in the engagement recess 40.

Specifically, a through hole 51 which communicates with the step difference portion 15 is formed at a nearly central part in the belt width direction L3 on a bottom wall surface of the engagement recess 40, and the biasing body 50 is exchangeably installed in the through hole 51. The biasing body 50 is a member formed in a block shape by using an elastic and insulating material, for example, hard plastic, silicon, polyurethane elastomer, or the like, and biases the engagement protrusion 36 by using its own elastic force.

In this case, the biasing body 50 is installed in the through hole 51, and thus biases the engagement protrusion 36 upward in the normal line direction L1. Accordingly, in the present embodiment, the biasing direction F of the biasing body 50 and the direction in which the engagement protrusion 36 is stored in the engagement recess 40, that is, the belt width direction L3 and the belt longitudinal direction L2 have a relationship of being perpendicular to each other.

In addition, the biasing body 50 installed in the through hole 51 is disposed so as to be pinched between the engagement protrusion 36 and the conductive belt 12, and thus biases the engagement protrusion 36 by also using an elastic force of the conductive belt 12.

Operation of Heart Rate Measurement Apparatus

Next, a description will be made of a case where the heart rate measurement apparatus 1 with the above-described configuration is attached to the chest of the user U so as to measure heart rate information of the user U.

In this case, first, the fixation belt 3 is turned around the chest of the user U, and, in this state, the apparatus main body 2 is temporarily pressed at an attachment position on the chest. In this state, as illustrated in FIG. 4, the engagement protrusions 36 of the connectors 30 provided at both ends of the fixation belt 3 in the longitudinal direction are inserted into the engagement recesses 40 of the apparatus main body 2 side in the belt width direction L3 so as to be engaged therewith. Accordingly, as illustrated in FIG. 1, the fixation belt 3 can be connected to the apparatus main body 2, and thus the apparatus main body 2 can be attached to the living body surface of the chest.

Subsequently, if the heart rate measurement apparatus 1 is operated, the pair of conductive belts 12 detects an electrocardiographic signal occurring due to heartbeats of the user U, and the detection circuit unit 26 starts measurement of electrocardiographic information such as a heart rate on the basis of the electrocardiographic signal.

Here, a detailed description will be made of the above-described connection between the fixation belt 3 and the apparatus main body 2.

If the engagement protrusion 36 is inserted into the engagement recess 40 in the belt width direction L3 through sliding, as illustrated in FIGS. 8 and 9, the stopper 37 formed at the connector 30 comes into contact with the outer wall surface of the second restraint wall 46 and is stored in the dent 41, and further sliding is restrained. Accordingly, the engagement protrusion 36 is positioned inside the engagement recess 40 in the belt width direction L3 so as to be engaged therewith.

Therefore, the fixation belt 3 can be connected to the apparatus main body 2, and thus the heart rate measurement apparatus 1 can be attached to the living body surface of the chest.

At this time, the biasing body 50 provided in the engagement recess 40 biases (the biasing direction F illustrated in FIG. 9) the engagement recess 40 in the normal line direction L1 different from the belt longitudinal direction L2, so as to maintain the engagement state between the engagement recess 40 and the engagement protrusion 36. For this reason, even if an external force such as a tensile force is applied to the fixation belt 3 during attachment, the belt longitudinal direction L2 is different from the biasing direction F, and thus it is possible to prevent looseness of the engagement recess 40 and the engagement protrusion 36.

Therefore, there is a low probability that looseness or abrupt detachment of the apparatus main body 2 may occur, and thus the apparatus main body 2 can be stably attached to the living body surface, unlike in the related art. Accordingly, it is possible to improve an attachment performance of the heart rate measurement apparatus 1, and to stably detect heart rate information with high accuracy by properly operating the apparatus main body 2.

Since the biasing direction F of the biasing body 50 and the direction in which the engagement protrusion 36 is stored in the engagement recess 40, that is, the belt width direction L3 and the belt longitudinal direction L2 have a relationship of being perpendicular to each other, it is possible to more effectively achieve the above-described operation and effect in which looseness or abrupt detachment of the apparatus main body 2 is reliably prevented.

If an external force is applied to the fixation belt 3 in the belt longitudinal direction L2 during attachment, as illustrated in FIGS. 10 to 12, the engagement protrusion 36 is deviated by an external force so as to be separated from the apparatus main body 2 in the belt longitudinal direction L2 inside the engagement recess 40, and is moved to the inside of the allowable space S. Then, the claw 36b of the engagement protrusion 36 comes into contact with the first restraint walls 45 and a further movement thereof is restrained, and thus the engagement protrusion 36 can be made to reliably remain in the allowable space S. In addition, at this time, the engagement protrusion 36 is restrained from being moved to the opened side of the engagement recess 40 by the second restraint wall 46. For this reason, it is possible to physically prevent the engagement protrusion 36 from being released out of the engagement recess 40.

As mentioned above, it is possible to further reliably prevent the apparatus main body 2 from being detached by reversely using the external force applied in the belt longitudinal direction L2.

In the present embodiment, since the biasing body 50 is pinched between the engagement protrusion 36 and the conductive belt 12 which is elastic, the engagement protrusion 36 can be biased by further using an elastic force of the conductive belt 12. Therefore, a biasing force can be adjusted without changing a size, a material, and the like of the biasing body 50 and without increasing the number of components, and thus the apparatus main body 2 can be more stably attached.

Since the biasing body 50 is exchangeably installed in the through hole 51, even if the biasing body 50 is worn out or the like, the biasing body 50 has only to be changed, and thus it is possible to reduce maintenance costs.

Modification Example

In the first embodiment, the biasing body 50 is exchangeably installed in the through hole 51 but is not limited to this case. For example, the biasing body 50 may be integrally formed with the case 10, and may be integrally formed with the conductive belt 12. However, preferably, the biasing body 50 is formed separately from the conductive belt 12, the case 10, or the like, and is exchangeably installed.

Second Embodiment

Next, a second embodiment according to the present invention will be described with reference to the drawings. In addition, in the second embodiment, the same constituent elements as those in the first embodiment are given the same reference numerals, and description thereof will not be repeated.

In the first embodiment, the engagement recess 40 is formed so as to be opened on the side surface side facing the belt longitudinal direction L2 in the outer wall 10A of the case 10, but, in the second embodiment, the engagement recess 40 is formed so as to be opened upward.

Configuration of Heart Rate Measurement Apparatus

As illustrated in FIGS. 13 and 14, in a heart rate measurement apparatus 60 of the present embodiment, an engagement recess 61 is formed so as to be opened upward in the outer wall 10A of the case 10. Therefore, the connector 30 of the fixation belt 3 side can be inserted into the engagement recess 61 through sliding in the belt width direction L3 in a state where the claw 36b faces downward.

In the present embodiment, the entire wall, which is located further outward in the belt longitudinal direction L2 than the engagement recess 61 in the outer wall 10A, functions as a first restraint wall 62. In addition, a second restraint wall 63 is formed so as to protrude toward the inside of the engagement recess 61 on the dent 41 side of the first restraint wall 62.

Operation of Heart Rate Measurement Apparatus

The heart rate measurement apparatus 60 with this configuration also can achieve the same operation and effect as in the first embodiment.

Third Embodiment

Next, a third embodiment according to the present invention will be described with reference to the drawings. In addition, in the third embodiment, the same constituent elements as those in the first embodiment are given the same reference numerals, and description thereof will not be repeated.

In the first embodiment, the biasing body 50 biases the engagement protrusion 36 in the normal line direction L1, but, in the third embodiment, the biasing body 50 biases the engagement protrusion 36 in the belt width direction L3.

Configuration of Heart Rate Measurement Apparatus

Figure 15:
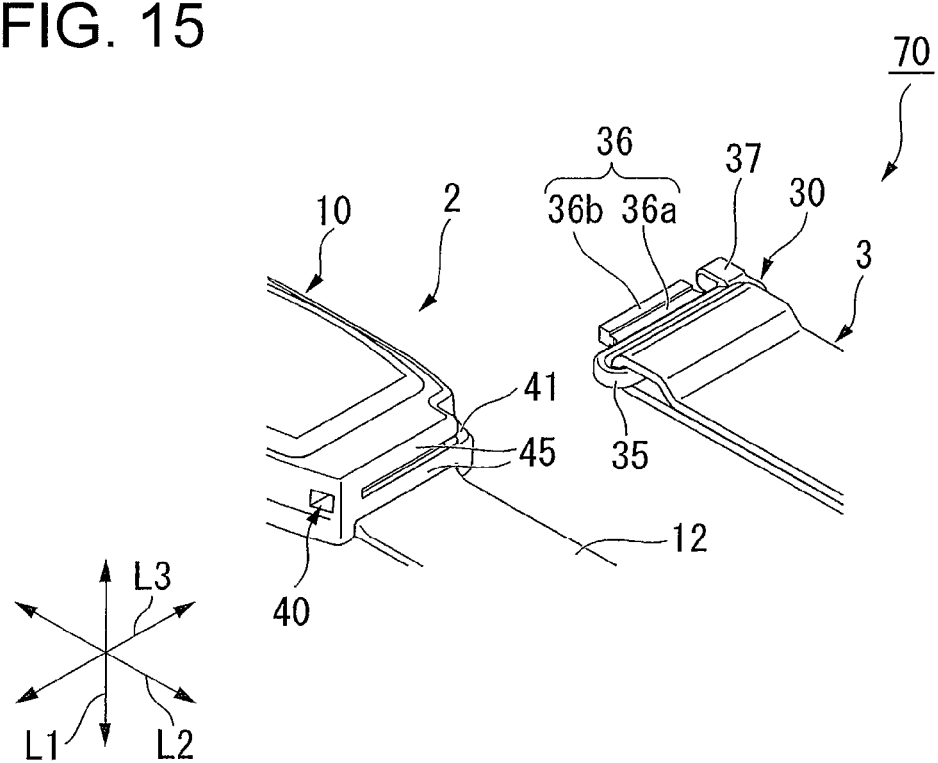
FIG. 15 is a diagram illustrating a third embodiment according to the present invention, and is a perspective view illustrating a state in which an apparatus main body is disconnected from a fixation belt.
Figure 16:
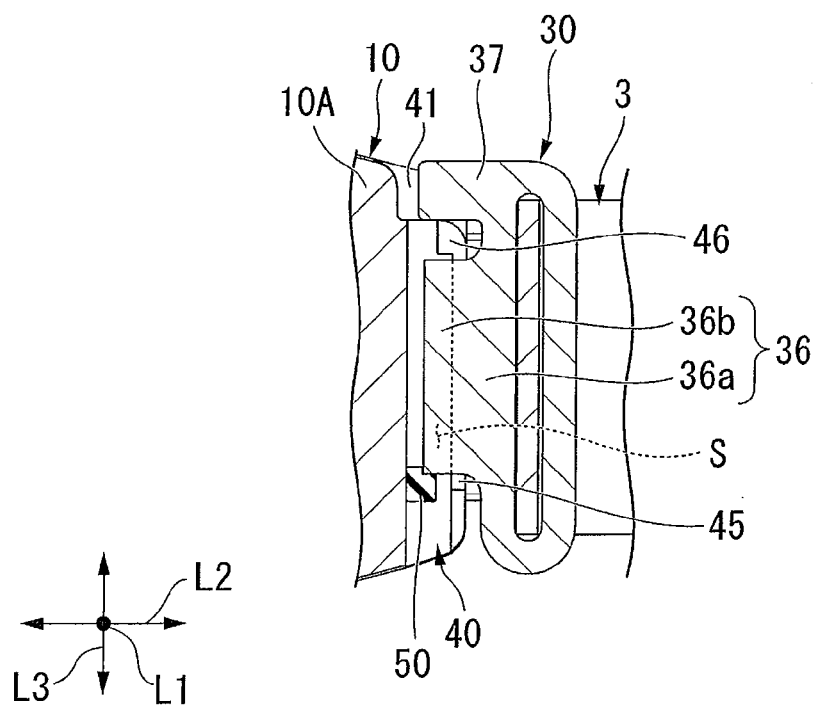
FIG. 16 is a cross-sectional view illustrating a state in which the apparatus main body and the fixation belt illustrated in FIG. 15 are connected to each other.

As illustrated in FIGS. 15 and 16, in a heart rate measurement apparatus 70 of the present embodiment, the biasing body 50 is installed in the engagement recess 40 on an opposite side to the second restraint wall 46 in the belt width direction L3 with the engagement protrusion 36 interposed therebetween, and biases the claw 36b of the engagement protrusion 36 toward the second restraint wall 46 side in the belt width direction L3.

Operation of Heart Rate Measurement Apparatus

In a case of the heart rate measurement apparatus 70 with this configuration, if the engagement protrusion 36 is inserted into the engagement recess 40 through sliding in the belt width direction L3, the biasing body 50 temporarily biases the engagement protrusion 36 so as to resist the sliding, but if the engagement protrusion 36 is deviated in the belt longitudinal direction L2 by an external force applied to the fixation belt 3 and is moved to the inside of the allowable space S, the claw 36b is pressed toward the inner wall surface of the second restraint wall 46 by a biasing force. For this reason, it is possible to reliably maintain an engagement state between the engagement recess 40 and the engagement protrusion 36 by using the pressing force.

As a result, in the same manner as in the first embodiment, looseness or abrupt detachment of the apparatus main body 2 can be prevented, and thus the apparatus main body 2 can be stably attached to the living body surface. Accordingly, it is possible to improve an attachment performance of the heart rate measurement apparatus 70, and to stably detect heart rate information with high accuracy.

Fourth Embodiment

Next, a fourth embodiment according to the present invention will be described with reference to the drawings. In addition, in the fourth embodiment, the same constituent elements as those in the first embodiment are given the same reference numerals, and description thereof will not be repeated.

In the first embodiment, the engagement protrusion 36 is inserted into the engagement recess 40 through sliding in the belt width direction L3, but, in the fourth embodiment, the engagement protrusion is fitted into the engagement recess in the normal line direction L1.

Configuration of Heart Rate Measurement Apparatus

Figure 17:
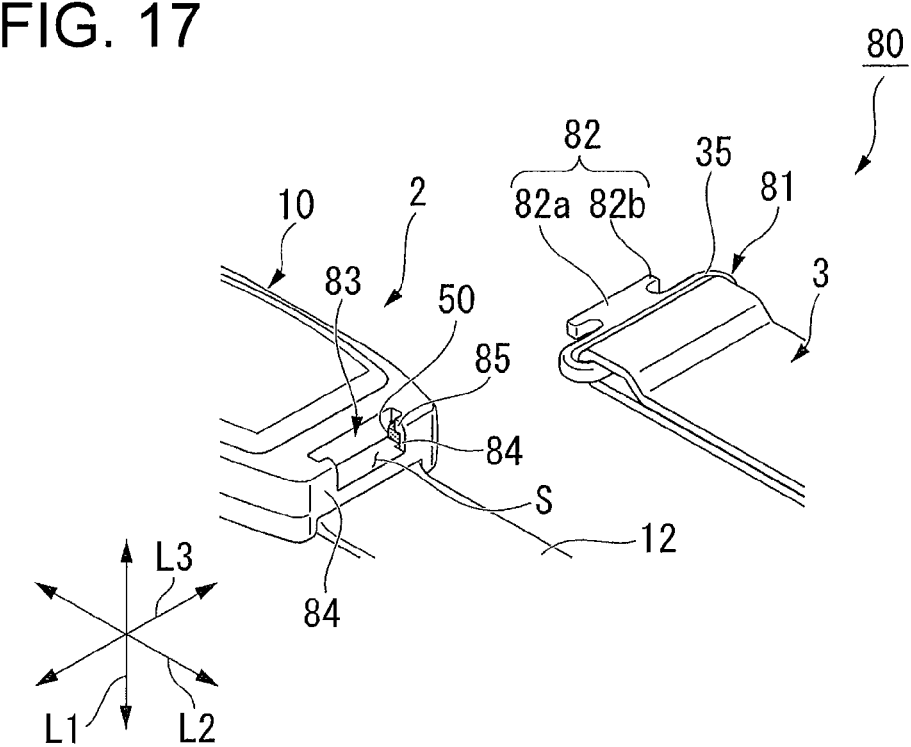
FIG. 17 is a diagram illustrating a fourth embodiment according to the present invention, and is a perspective view illustrating a state in which an apparatus main body is disconnected from a fixation belt.
Figure 18:
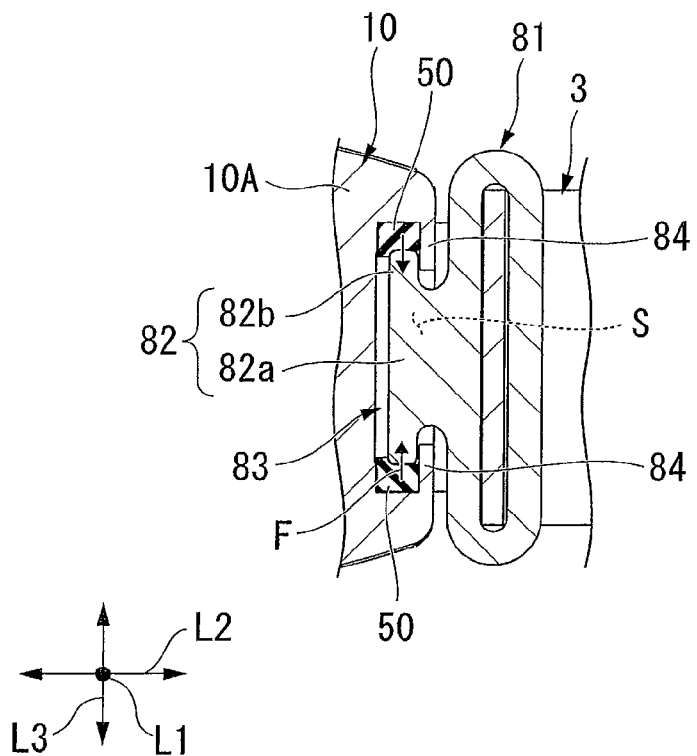
FIG. 18 is a cross-sectional view illustrating a state in which the apparatus main body and the fixation belt illustrated in FIG. 17 are connected to each other.

As illustrated in FIGS. 17 and 18, a heart rate measurement apparatus 80 of the present embodiment includes a connector 81 having an engagement protrusion 82 which protrudes toward the apparatus main body 2 in the belt longitudinal direction L2 from the annular ring 35. In addition, in the present embodiment, the stopper 37 in the first embodiment is not provided.

The engagement protrusion 82 of the present embodiment is a member which is detachably stored in an engagement recess 83 described later formed at the apparatus main body 2 side by being fitted thereinto in the normal line direction L1.

Specifically, the engagement protrusion 82 includes a protrusion piece 82a whose base end is integrally formed with the annular ring 35 and which protrudes in the belt longitudinal direction L2, and a pair of claws 82b which protrudes in the belt width direction L3 from a front end of the protrusion piece 82a. The engagement protrusion 82 is formed in a T shape in a plan view.

Meanwhile, the engagement recess 83 which is opened in a side surface and an upper surface facing the belt longitudinal direction L2 is formed at the outer wall 10A of the case 10 of the apparatus main body 2 so as to correspond to the shape of the engagement protrusion 82. Accordingly, the engagement protrusion 82 can be fitted into the engagement recess 83 in the normal line direction L1 so as to be stored therein.

In addition, the allowable space S which allows the engagement protrusion 82 to be moved in the belt longitudinal direction L2 is also formed in the engagement recess 83 of the present embodiment. Further, a first restraint wall 84 and a second restraint wall 85 are formed at the outer wall 10A of the case 10. The first restraint walls 84 restrain the claws 82b of the engagement protrusion 82 moved in the allowable space S from being further moved in the belt longitudinal direction L2 so as to make the engagement protrusion 82 remain in the allowable space S, and the second restraint wall 85 restrains the claws 82b from being moved toward the opened side of the engagement recess 83.

In addition, a pair of biasing bodies 50, which biases the pair of claws 82b of the engagement protrusion 82 stored in the engagement recess 83 in the belt width direction L3, is provided in the engagement recess 83. The pair of biasing bodies 50 biases the claws 82b so as to pinch the engagement protrusion 82 from both sides in the belt width direction L3 (the biasing direction F illustrated in FIG. 18).

Operation of Heart Rate Measurement Apparatus

In the heart rate measurement apparatus 80 of the present embodiment, if the engagement protrusion 82 is fitted into the engagement recess 83 in the normal line direction L1, the biasing bodies 50 bias the engagement protrusion 82 in the belt width direction L3 different from the belt longitudinal direction L2 so that the engagement protrusion 82 is interposed between both sides of the biasing bodies in the belt width direction L3, thereby maintaining an engagement state between the engagement recess 83 and the engagement protrusion 82.

For this reason, even if an external force such as a tensile force is applied to the fixation belt 3 during attachment, the belt longitudinal direction L2 is different from the biasing direction F, and thus it is possible to maintain an engagement state between the engagement recess 83 and the engagement protrusion 82. Therefore, it is possible to prevent looseness or abrupt detachment of the apparatus main body 2.

In addition, even if an external force is applied to the fixation belt 3 in the belt longitudinal direction L2 during attachment, the claws 82b of the engagement protrusion 82 come into contact with the first restraint walls 84 at the time when the engagement protrusion 82 is moved to the inside the allowable space S, and further movement thereof is restrained. Thus, the engagement protrusion 82 can be made to reliably remain in the allowable space S. In addition, at this time, the engagement protrusion 82 is restrained from being moved to the opened side of the engagement recess 83 by the second restraint wall 85. For this reason, it is possible to physically prevent the engagement protrusion 82 from being released out of the engagement recess 83.

Therefore, also in the present embodiment, it is possible to reliably prevent the apparatus main body 2 from being detached by reversely using the external force applied in the belt longitudinal direction L2.

Modification Example

In addition, in the fourth embodiment, the pair of biasing bodies 50 is provided in the engagement recess 83 so that the engagement protrusion 82 is interposed between both sides thereof in the belt width direction L3, but the biasing body 50 may be used singly. Even in this case, the engagement protrusion 82 can be biased in the belt width direction L3 so as to be pressed toward the inner surface of the engagement recess 83, and an engagement state between the engagement protrusion 82 and the engagement recess 83 can be maintained by using the pressing force.

Fifth Embodiment

Next, a fifth embodiment according to the present invention will be described with reference to the drawings. In addition, in the fifth embodiment, the same constituent elements as those in the fourth embodiment are given the same reference numerals, and description thereof will not be repeated.

In the fourth embodiment, the biasing body 50 biases the engagement protrusion 82 in the belt width direction L3, but, in the fifth embodiment, the biasing body 50 biases the engagement protrusion 82 in the normal line direction L1.

Configuration of Heart Rate Measurement Apparatus

As illustrated in FIGS. 19 and 20, in a heart rate measurement apparatus 90 of the present embodiment, in the same manner as in the first embodiment, a through hole 51 is formed on a bottom wall surface of the engagement recess 83, and the biasing body 50 is installed in the through hole 51. In this case, the biasing body 50 is installed so as to be pinched between the conductive belt 12 and the engagement protrusion 82.

Operation of Heart Rate Measurement Apparatus

In a case of the heart rate measurement apparatus 90 with this configuration, if the engagement protrusion 82 is fitted into the engagement recess 83 in the normal line direction L1, the biasing body 50 temporarily biases the engagement protrusion 82 so as to resist the fitting, but if the engagement protrusion 82 is deviated in the belt longitudinal direction L2 by an external force applied to the fixation belt 3 and is moved to the inside of the allowable space S, the claws 82b are pressed toward the inner wall surface of the second restraint wall 85 by a biasing force. For this reason, it is possible to reliably maintain an engagement state between the engagement recess 83 and the engagement protrusion 82 by using the pressing force.

Therefore, also in the present embodiment, looseness or abrupt detachment of the apparatus main body 2 can be prevented.

Sixth Embodiment

Next, a sixth embodiment according to the present invention will be described with reference to the drawings. In addition, in the sixth embodiment, the same constituent elements as those in the first embodiment are given the same reference numerals, and description thereof will not be repeated.

In the first embodiment, the biasing body 50 biases the engagement protrusion 36 in the normal line direction L1, but, in the sixth embodiment, the biasing body 50 biases the engagement protrusion 36 in the belt longitudinal direction L2.

Configuration of Heart Rate Measurement Apparatus

Figure 21:
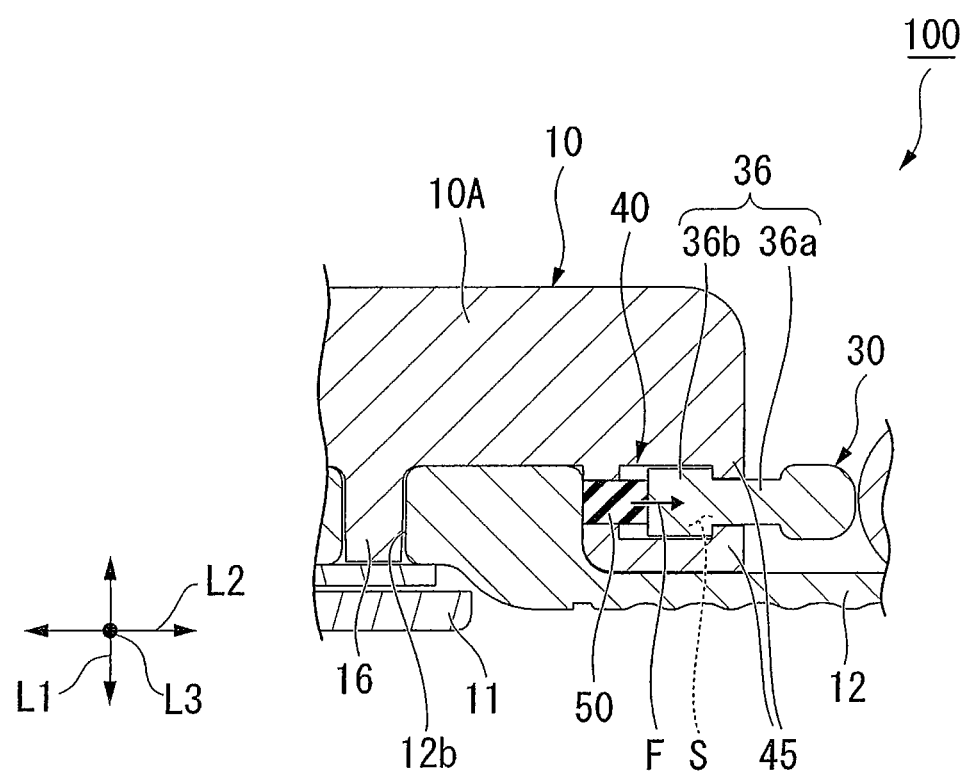
FIG. 21 is a diagram illustrating a sixth embodiment according to the present invention, and is a cross-sectional view illustrating a state in which an apparatus main body and a fixation belt are connected to each other.

As illustrated in FIG. 21, in a heart rate measurement apparatus 100 of the present embodiment, the biasing body 50 is installed on the outer wall 10A side of the case 10 in the engagement recess 40, and biases the claw 36b of the engagement protrusion 36 toward the first restraint wall 45 side in the belt longitudinal direction L2.

Operation of Heart Rate Measurement Apparatus

In a case of the heart rate measurement apparatus 100 with this configuration, if the engagement protrusion 36 is inserted into the engagement recess 40 through sliding in the belt width direction L3, the biasing body 50 biases the engagement protrusion 36 in the belt longitudinal direction L2. The engagement protrusion 36 is deviated in the belt longitudinal direction L2 and is moved to the inside of the allowable space S by the biasing force. The biasing body 50 presses the engagement protrusion 36 toward the first restraint wall 45 even in a state in which the engagement protrusion 36 has been moved to the inside of the allowable space S. For this reason, it is possible to reliably maintain an engagement state between the engagement recess 40 and the engagement protrusion 36 by using the pressing force.

Further, in the present embodiment as well, the biasing body 50 biases the engagement protrusion 36 by also using an elastic force of the conductive belt 12, and thus it becomes easier to more reliably maintain an engagement state with the engagement recess 40.

In addition, the engagement protrusion 36 is restrained from being reversely moved and being moved toward the opened side of the engagement recess 40 by the second restraint wall 46 (refer to FIG. 7) and the biasing body 50 at the time when the engagement protrusion 36 is moved to the inside the allowable space S. For this reason, it is possible to physically prevent the engagement protrusion 36 from being released out of the engagement recess 40.

As a result, in the same manner as in the first embodiment, looseness or abrupt detachment of the apparatus main body 2 can be prevented, and thus the apparatus main body 2 can be stably attached to the living body surface. Accordingly, it is possible to improve an attachment performance of the heart rate measurement apparatus 100, and to stably detect heart rate information with high accuracy.

The technical scope of the present invention is not limited to the embodiments, and various modifications may be added thereto in the scope without departing from the spirit of the present invention.

For example, in the embodiments, a portable electronic apparatus has been described by exemplifying a heart rate measurement apparatus, but is not limited to this case, and may be, for example, a pedometer, a stopwatch, or the like. In other words, any electronic apparatus may be used as long as the electronic apparatus can be attached to a living body surface of a user and be used.

In addition, in the respective embodiments, the connectors having the engagement protrusions are provided at both ends of the fixation belt in the longitudinal direction, but are not limited to this case. For example, one end of the fixation belt in the longitudinal direction may be integrally formed with the case of the apparatus main body, and the connector may be provided only at the other end of the fixation belt in the longitudinal direction.

In addition, as described in the respective embodiments, any method of installing the biasing body may be employed as long as the biasing body biases the engagement protrusion so as to prevent looseness of the engagement protrusion and the engagement recess.

However, preferably, the biasing body biases the engagement protrusion in a direction different from a belt longitudinal direction, and, more preferably, a biasing direction of the biasing body, a direction in which the engagement protrusion is stored in the engagement recess, and the belt longitudinal direction have a relationship of being perpendicular to each other.

In the present embodiments, the engagement protrusion 36 is provided at the connector 30, and the engagement recess 40 is provided at the apparatus main body 2, but the present invention is not limited thereto. For example, the engagement protrusion 36 may be provided at the apparatus main body 2, and the engagement recess 40 may be provided at the connector 30.

In addition, the biasing body 50 may be provided at either of the engagement protrusion 36 and the engagement recess 40.

What is claimed is:
1. A portable electronic apparatus comprising:
an apparatus main body that includes electronic components built therein;
a fixation belt configured to attach the apparatus main body to a living body surface;
a connector that is provided at a longitudinal end of the fixation belt;
an engagement recess that is formed at one of the apparatus main body and the connector;
an engagement protrusion that is formed at the other of the apparatus main body and the connector and is detachably storable in the engagement recess, wherein a relative position between the engagement recess and the connector stored in the engagement recess is defined by three orthogonal axes extending in (i) a longitudinal direction parallel to a longitudinal direction of the fixation belt, (ii) a transverse direction parallel to a transverse direction of the fixation belt and (iii) a thickness direction parallel to a thickness of the fixation belt;

a biasing body that is provided in the engagement recess, and arranged to urge the engagement protrusion stored in the engagement recess so as to maintain the engagement recess and the engagement protrusion in engagement with each other; and a pair of electrode members that is installed at the apparatus main body so as to be in contact with the living body surface, wherein the electronic components comprise a biological information detection unit operable to detect a potential difference across the pair of electrode members and translate the potential difference into biological information, wherein each of the electrode members is made of an elastic material, and the biasing body is sandwiched between the engagement protrusion stored in the engagement recess and one of the electrode members.

2. The portable electronic apparatus according to claim 1, wherein the engagement recess comprises an allowable space therein that allows the engagement protrusion stored in the engagement recess to move in the a longitudinal direction within the engagement recess, and wherein the engagement recess includes:

a first restraint wall configured to regulate movement of the engagement protrusion in the allowable space in the longitudinal direction; and a second restraint wall configured to regulate movement of the engagement protrusion in the allowable space in the transverse direction.

3. The portable electronic apparatus according to claim 2, wherein the biasing body urges the engagement protrusion stored in the engagement recess in the transverse direction.

4. The portable electronic apparatus according to claim 1, wherein the biasing body urges the engagement protrusion stored in the engagement recess in a direction different from the longitudinal direction.

5. The portable electronic apparatus according to claim 1, wherein a biasing direction of the biasing body, a direction in which the engagement protrusion is stored in the engagement recess, and the longitudinal direction have a relationship of being perpendicular to each other.

6. The portable electronic apparatus according to claim 1, wherein the biasing body is replaceably provided in the engagement recess.

7. The portable electronic apparatus according to claim 1, wherein the biasing body is arranged to urge the engagement protrusion stored in the engagement recess in an upper direction of the thickness direction.

8. The portable electronic apparatus according to claim 1, wherein the biasing body is arranged to urge the engagement protrusion stored in the engagement recess in the transverse direction.

9. The portable electronic apparatus according to claim 8, wherein the biasing body comprises a pair of biasing members arranged to pinch the engagement protrusion stored in the engagement recess in the transverse direction.

10. The portable electronic apparatus according to claim 1, wherein the biasing body is arranged to urge the engagement protrusion stored in the engagement recess in the longitudinal direction.

* * * * *